US010093984B2

(12) United States Patent
Ibáñez de Cáceres et al.

(10) Patent No.: US 10,093,984 B2
(45) Date of Patent: Oct. 9, 2018

(54) PROBE FOR DETECTING AND/OR QUANTIFYING METHYLATION OF THE PROMOTER OF THE IGFBP-3 GENE

(71) Applicants: FUNDACIÓN PARA LA INVESTIGACIÓN BIOMÉDICA DEL HOSPITAL UNIVERSITARIO LA PAZ, Madrid (ES); CONSEJO SUPERIOR DE INVESTIGACIONES CIENTÍFICAS (CSIC), Madrid (ES); UNIVERSIDAD AUTÓNOMA DE MADRID, Madrid (ES); FUNDACIÓN HOSPITAL DE MADRID, Madrid (ES)

(72) Inventors: Inmaculada Ibáñez de Cáceres, Madrid (ES); Olga Pernía Arias, Madrid (ES); Cristóbal Belda Iniesta, Madrid (ES); Rosario Perona Abellón, Madrid (ES); María Cortés Sempere, Madrid (ES)

(73) Assignees: FUNDACIÓN PARA LA INVESTIGACIÓN BIOMÉDICA DEL HOSPITAL UNIVERSITARIO LA PAZ, Madrid (ES); CONSEJO SUPERIOR DE INVESTIGACIONES CIENTÍFICAS (CSIC), Madrid (ES); UNIVERSIDAD AUTÓNOMA DE MADRID, Madrid (ES); FUNDACIÓN HOSPITAL DE MADRID, Madrid (ES)

( * ) Notice: Subject to any disclaimer, the term of this patent is extended or adjusted under 35 U.S.C. 154(b) by 131 days.

(21) Appl. No.: 14/894,172

(22) PCT Filed: May 27, 2014

(86) PCT No.: PCT/ES2014/070433
§ 371 (c)(1),
(2) Date: Nov. 25, 2015

(87) PCT Pub. No.: WO2014/191600
PCT Pub. Date: Dec. 4, 2014

(65) Prior Publication Data
US 2016/0122828 A1   May 5, 2016

(30) Foreign Application Priority Data

May 29, 2013 (ES) .................................. 201330783

(51) Int. Cl.
*C07H 21/02* (2006.01)
*C07H 21/04* (2006.01)
*C12Q 1/6886* (2018.01)

(52) U.S. Cl.
CPC ..... *C12Q 1/6886* (2013.01); *C12Q 2600/106* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| 6,312,922 | B1* | 11/2001 | Edwards | ................ | C07K 14/47 |
| | | | | | 435/252.3 |
| 2003/0143606 | A1* | 7/2003 | Olek | .................. | C07K 14/4703 |
| | | | | | 435/6.12 |
| 2004/0005294 | A1 | 1/2004 | Lee | | |

OTHER PUBLICATIONS

NCBI Database. GenBank Accession No. AM488980, Feb. 5, 2008,(National Center for Biotechnology Information, National Library of Medicine (Bethesda, MD, USA)).*
NCBI Database (GenBank Accession No. XM_641611, Jan. 29, 2010 (National Center for Biotechnology Information, National Library of Medicine (Bethesda, MD, USA)).*
Ibanez de Caceres et al (Oncogene. 2010. 29: 1681-1690 and Supplemental Table 1.*
Supplementary European Search Report dated Dec. 5, 2016, Appln No. EP 14804898.
Cortes-Sempere, et al., "IGFBP-3 methylation-derived deficiency mediates the resistance to cisplatin through the activation of the IGFIR/Akt pathway in non-small cell lung cancer", Oncogene vol. 32, (2013), 1274-1283.
Pernia, et al., "Methylation status of IGFBP-3 as a useful clinical tool for deciding on a concomitant radiotherapy", Epigenetics vol. 9, Issue 11, (Nov. 2014), 1446-1453.
Sun, Yunguang , et al., "Role of Insulin-Like Growth Factor-1 Signaling Pathway in Cisplatin-Resistant Lung Cancer Cells", International Journal of Radiation Oncology Biology Physics, vol. 82, No. 3, (2012), e563-e572.
PCT International Search Report and Written Opinion dated Sep. 12, 2014, PCT/ES2014/070433, with English-language translations, 18 pages.
Bradley, J. D., et al., "Primary Analysis of the Phase II Component of a Phase I/II Dose Intensification Study Using Three-Dimensional Conformal Radiation Therapy and Concurrent Chemotherapy for Patients With Inoperable Non-Small-Cell Lung Cancer: RTOG 0117", *Journal of Clinical Oncology*, vol. 28, No. 14, (2010), 2475-2480.

(Continued)

*Primary Examiner* — Carla J Myers
(74) *Attorney, Agent, or Firm* — Womble Bond Dickinson (US) LLP

(57) ABSTRACT

The invention relates to a method to predict the response to treatment with radiotherapy combined with cisplatin-based chemotherapy in patients with cancer, preferably non-microcytic lung cancer, wherein said method is based on the detection of the presence of methylation in the IGFBP-3 gene. The present invention also relates to an in vitro method to design a customised treatment for an individual with said disease. The method of the invention may be quantitative or semi-quantitative. The present invention also relates to a probe designed for the quantitative detection of the methylation of the IGFBP-3 gene, to a kit that comprises it and to the use of the kit to predict the response of a subject to the aforementioned treatment.

1 Claim, 5 Drawing Sheets
Specification includes a Sequence Listing.

(56) References Cited

OTHER PUBLICATIONS

Chang, Y. S., et al., "Clinical Significance of Insulin-like Growth Factor-binding Protein-3 Expression in Stage I Non-Small Cell Lung Cancer", *Clinical Cancer Research,* vol. 8, No. 12, (2002), 3796-3802.

Chang, Y. S., et al., "Correlation between Insulin-like Growth Factor-binding Protein-3 Promoter Methylation and Prognosis of Patients with Stage I Non-Small Cell Lung Cancer", *Clinical Cancer Research,* vol. 8, No. 12, (2002), 3669-3675.

Cubbage, M. L., et al., "Insulin-like Growth Factor Binding Protein-3: Organization of the Human Chromosomal Gene and Demonstration of Promoter Activity", *The Journal of Biological Chemistry,* vol. 265, No. 21, (1990), 12642-12649.

Curran Jr., W. J., et al., "Sequential vs Concurrent Chemoradiation for Stage III Non-Small Cell Lung Cancer: Randomized Phase III Trial RTOG 9410", *Journal of National Cancer Institute,* vol. 103, No. 19, (2011), 1452-1460.

Ibanez De Caceres, I., et al., "Identification of Novel Target Genes by an Epigenetic Reactivation Screen of Renal Cancer", *Cancer Research,* vol. 66, (2006), 5021-5028.

Ibanez De Caceres, I., et al., "IGFBP-3 hypermethylation-derived deficiency mediates cisplatin resistance in non-small-cell lung cancer", *Oncogene,* vol. 29, No. 11, (2010), 1681-1690.

Moreno-Jimenez, M., et al., "Radioterapia combinada con quimioterapia en el tratamiento del cáncer de pulmón", *Rev Med Univ Navarra,* vol. 51, No. 4, (2007), 13-33.

Tomii, K., et al., "Aberrant promoter methylation of insulin-like growth factor binding protein-3 gene in human cancers", *International Journal of Cancer,* vol. 120, No. 3, (2007), 566-573.

Torng, P.-L., et al., "Promoter methylation of IGFBP-3 and p53 expression in ovarian endometrioid carcinoma", *Molecular Cancer,* 8:120, (2009), 12 pages.

\* cited by examiner

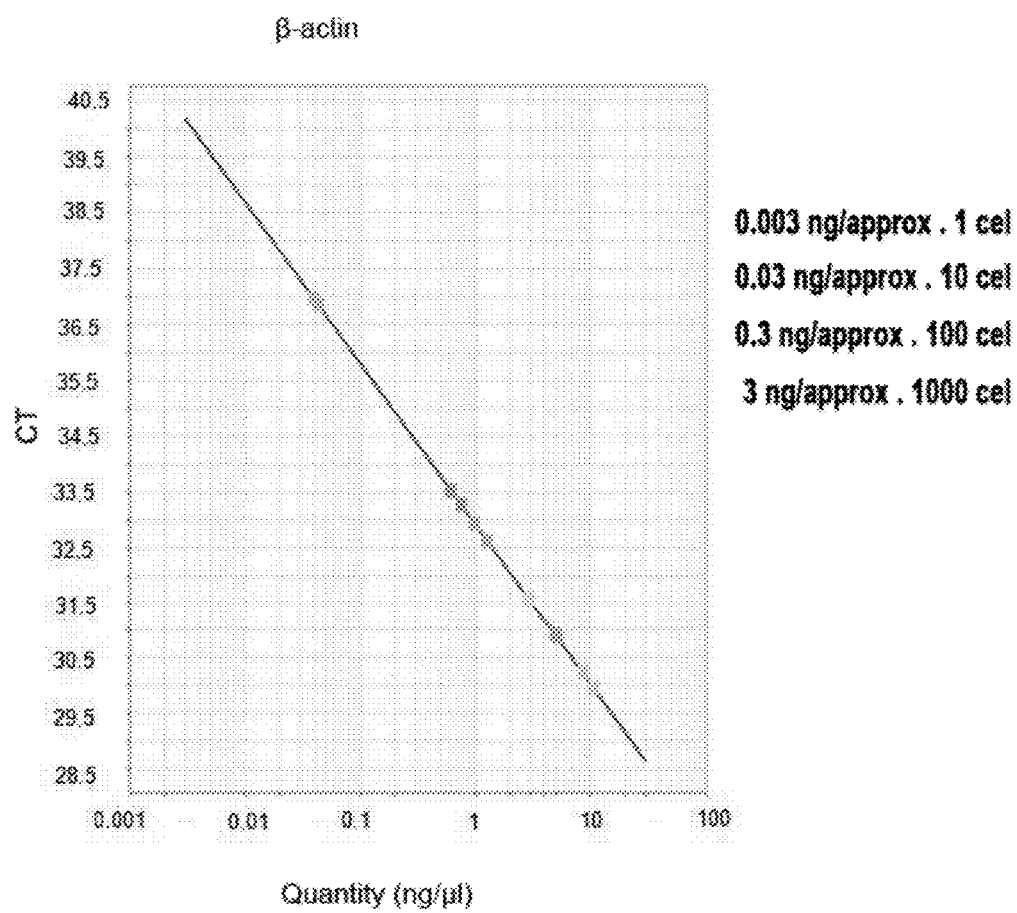

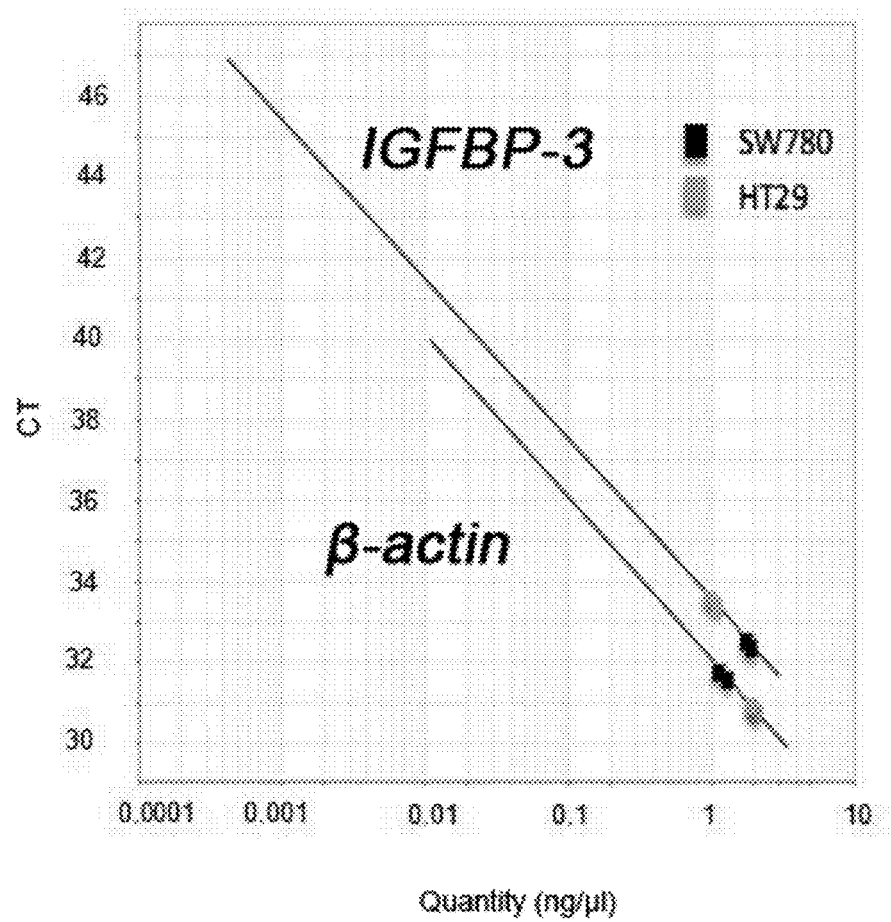

SEQUENCE LISTING

<160> NUMBER OF SEQ ID NOS: 7

<210> SEQ ID NO 1
<211> LENGTH: 688
<212> TYPE: DNA
<213> ORGANISM: Homo sapiens

<400> SEQUENCE: 1

```
agcccagcgg gtgtaaatta aaccccgcag tgccttggct ccctgagacc caaatgtaag      60
tcagaaatgt cccaagactt cgcctgccaa cggaattaaa ttttagaaag ctccacgagg     120
tacacacgaa tgcggagcgc tgtatgccag tttccccgac accggctcgc cgcagggaga     180
cctcaccccg agagcggaag gggtaagggc ggcggggtca aggagatcgg gggtgctgag     240
```

```
ttggccagga gtgactgggg tgaccggggg tgctgaggtg gcctggagtg ccggggtggc    300
cgggcacacc ttggttcttg tagacgacaa ggtgacccgg gctccgggcg tgcgcacgag    360
gagcaggtgc ccgggcgagt ctcgagctgc acgcccccga gctcggcccc ggctgctcag    420
ggcgaagcac gggcccccgc agccgtgcct cgccgaccc gccccctcc caaccccac      480 tcctgggcgc gccgttccgg ggcgtgtcct gggccacccc ggcttctata tagcggccgg    540
cgcgcccggg ccgcccagat gcgagcactg cggctgggcg ctgaggatca gccgcttcct    600
gcctggattc cacagcttcg cgccgtgtac tgtcgcccca tccctgcgcg cccagcctgc    660
caagcagcgt gccccggttg caggcgtc                                       688

<210> SEQ ID NO 2
<211> LENGTH: 92
<212> TYPE: DNA
<213> ORGANISM: Homo sapiens

<400> SEQUENCE: 2
agaaagctcc acgaggtaca cacgaatgcg gagcgctgta tgccagtttc cccgacaccg    60
gctcgccgca gggagacctc accccgagag cg                                  92

<210> SEQ ID NO 3
<211> LENGTH: 23
<212> TYPE: DNA
<213> ORGANISM: Artificial Sequence
<220> FEATURE:
<223> OTHER INFORMATION: Sense primer for the detection of methylated
      IGFBP3 gene

<400> SEQUENCE: 3
ttttacgagg tatatacgaa tgc                                            23

<210> SEQ ID NO 4
<211> LENGTH: 23
<212> TYPE: DNA
<213> ORGANISM: Artificial Sequence
<220> FEATURE:
<223> OTHER INFORMATION: Antisense primer for the detection of
      methylated IGFBP3 gene

<400> SEQUENCE: 4
tctcgaaata aaatctccct acg                                            23

<210> SEQ ID NO 5
<211> LENGTH: 25
<212> TYPE: DNA
<213> ORGANISM: Artificial Sequence
<220> FEATURE:
<223> OTHER INFORMATION: Sense primer for the detection of
      non-methylated IGFBP3 gene

<400> SEQUENCE: 5
agaaagtttt atgaggtata tatga                                          25

<210> SEQ ID NO 6
<211> LENGTH: 23
<212> TYPE: DNA
<213> ORGANISM: Artificial Sequence
<220> FEATURE:
<223> OTHER INFORMATION: Antisense primer for the detection of
      non-methylated IGFBP3 gen

<400> SEQUENCE: 6
cactctcaaa ataaaatctc cct                                            23
```

```
<210> SEQ ID NO 7
<211> LENGTH: 17
<212> TYPE: DNA
<213> ORGANISM: Artificial Sequence
<220> FEATURE:
<223> OTHER INFORMATION: Probe for the detection of methylated IGFBP3
      gene

<400> SEQUENCE: 7
ccgatatcga aaaaact                                                    17
```

PROBE FOR DETECTING AND/OR QUANTIFYING METHYLATION OF THE PROMOTER OF THE IGFBP-3 GENE

CROSS-REFERENCE TO RELATED APPLICATIONS

The present patent application is a national phase application of International Application No. PCT/ES2014/070433, filed May 27,2014, which claims priority to Spanish Application No. P201330783, filed May 29,2013, the disclosures of which are incorporated herein by reference.

The present invention relates to a method to predict the response to treatment with radiotherapy combined with cisplatin-based chemotherapy in patients with cancer, preferably non-microcytic lung cancer, where said method is based on the detection of the presence of methylation in the IGFBP-3 gene. The method of the invention may be quantitative or semi-quantitative. The present invention also relates to a probe for the quantitative detection of methylation in the IGFBP-3 gene. Therefore, the invention falls within the field of cancer treatment.

PRIOR STATE OF THE ART

Combined radiotherapy and chemotherapy in a patient with cancer makes it possible to combine the benefits of both techniques and has allowed for increased survival in various types of cancer, for example, lung cancer; however, there is greater toxicity with said treatment (Moreno-Jiménez M. et al. Rev Med Univ Navarra 51(4):13-33).

In chemotherapy, cisplatin, also called cis-diaminodichloroplatinum (II) (CDDP), is the treatment of choice for various types of cancers, including non-microcytic lung cancer. Cisplatin may be administered in therapy combined with radiotherapy, since multi-centre studies have shown a better overall response (Curran W. J., Jr. et al. 2011 Journal of the National Cancer Institute 103:1452-60).

It has been described that platinum-based chemotherapeutic agents, including cisplatin, cause the de novo promoter methylation of certain genes, thereby altering the expression thereof. Said genes include the gene that encodes the insulin-like growth factor binding protein (IGFBP-3) (Ibáñez de Cáceres I. et al. 2010 Oncogene 29:1681-90).

Hypermethylation of the 5' promoter region of the IGFBP-3 gene is an epigenetic process that takes place very frequently in human cancer (40%-60%) (Chang Y. S. et al. 2002 Clin Cancer Res 8:3796-802; Ibáñez de Cáceres I. et al. 2010 Oncogene 29:1681-90; Torng P. L. et al. 2009 Mol Cancer 8:120). Methylation of the IGFBP-3 gene may be detected using different techniques, such as, for example, bisulfite sequencing and the methylation-specific polymerase chain reaction (PCR) assay (MSP) (Ibáñez de Cáceres I. et al. 2010 Oncogene 29:1681-90; Tomii K. et al. 2007 Int J Cancer 120:566-73; Ibáñez de Cáceres I. et al. 2006 Cancer Res 66:5021-8).

At present, there is a clinical need to determine whether or not a patient will respond to a combined chemotherapy and radiotherapy treatment in order to adapt the treatment to each individual case, and thus prevent the secondary effects associated with the toxicity of the combined therapy and prevent overtreatment in patients who are not going to respond to it.

DESCRIPTION OF THE INVENTION

The technical problem solved by the invention is that it provides a method to predict the response of a subject to treatment with radiotherapy combined with platinum-based chemotherapy.

The present invention shows that the detection and/or quantification of the promoter region of the IGFBP-3 gene, specifically, the region between positions −584 and −492 of the promoter (positions numbered from the ATG initiator), is useful to predict the response of a subject with cancer to treatment with radiotherapy combined with platinum-based chemotherapy, as well as to design an individualised treatment for the subject.

The method of the invention may be performed by using primer pairs that detect the presence of methylation and/or primer pairs that detect the absence of methylation, which in the present invention is called "semi-quantitative" detection. Moreover, it may also be performed by using a probe, which allows for "quantitative" detection. The studies that demonstrate the invention were performed both in cell lines and in surgical samples from patients.

Moreover, the inventors have demonstrated that the use of a probe that detects positions −532 and −526 of the IGFBP-3 gene promoter makes it possible to quantify the degree of methylation of said gene. The use of the probe described in the invention makes it possible to predict whether or not a subject with cancer will respond to a combined treatment with platinum-based chemotherapy and radiotherapy with greater sensitivity and efficacy.

As herein described, a first aspect of the invention relates to a method to obtain useful data to predict the response of a subject with cancer to treatment with radiotherapy combined with cisplatin-based chemotherapy, which comprises detecting and/or quantifying the promoter methylation of the IGFBP-3 gene in a biological sample from said subject.

In the present invention, the cancer is preferably lung cancer, ovarian cancer, head and neck cancer, glioma and breast cancer. More preferably, the lung cancer is non-microcytic lung cancer.

The terms "non-microcytic lung cancer", "non-microcytic pulmonary cancer", "non-microcytic lung carcinoma" (NMLC), "non-microcytic pulmonary carcinoma" (NMPC) and "non-small cell lung cancer" (NSCLC) refer to a type of lung cancer or tumour that, according to the histological classification, comprises the subtypes squamous or epidermoid carcinoma, adenocarcinoma, adenosquamous carcinoma, sarcomatoid carcinoma and large-cell carcinoma.

"Treatment" is understood to mean the set of means used to cure or relieve an illness.

In the present invention, "treatment with radiotherapy combined with cisplatin-based chemotherapy" is understood to mean the sequential treatment that comprises, in the first place, treatment with cisplatin-based chemotherapy and, subsequently, treatment with radiotherapy in accordance with the specific criteria for each case known to persons skilled in the art.

In the present invention, the chemotherapy may also be based on other platinum-derived drugs, such as, for example, carboplatin, oxaliplatin, satraplatin and picoplatin.

"Promoter methylation" is understood to mean the presence of methyl groups at the 5' positions of the cytosines of the CpG island located before and next to a guanine (i.e. of a CG dinucleotide) in a gene promoter.

"Hypermethylation" is understood to mean an increase in promoter methylation with respect to values considered to be normal by persons skilled in the art. "Hypomethylation" is understood to mean a decrease in promoter methylation with respect to values considered to be normal by persons skilled in the art.

In the present invention, "CpG island" is understood to mean the gene promoter region that contains at least 500 base pairs, a proportion of CG dinucleotides (cytosine-guanine) greater than 50%.

In the present invention, "promoter" or "promoter region" is understood to mean a nucleotide sequence that controls the transcription of a given gene; in the present invention, it is the IGFBP-3 gene.

In the present invention, the IGFBP-3 (or IGFBP3) gene is defined as the gene that encodes the insulin-like growth factor binding protein. Said gene (Entrez ID: 3486) is located in the 7p12.3 chromosomal region and encodes two alternative transcripts that share the same promoter, NM_000598.4 and NM_001013398.1. The CpG island of the IGFBP-3 gene is located at position −518/+744 with respect to the first exon and encompasses 688 base pairs above the ATG site, including the gene promoter described (SEQ ID NO: 1).

In the present invention, the detection and/or quantification may be performed by any method known to persons skilled in the art, such as, for example, without being limited thereto, polymerase chain reaction (PCR), methylation-specific PCR (MSP), quantitative MSP (QMSP or qMSP) or sequencing. The DNA may have been subjected to a reaction with bisulfite prior to its detection and/or quantification.

The term "biological sample" includes, without being limited thereto, biological tissues and/or fluids from an individual, obtained by any method designed for that purpose known to persons skilled in the art. The biological sample comprises deoxyribonucleic acid (DNA). Said DNA may or may not be methylated and may present different degrees of methylation.

In the present invention, the terms "subject", "individual" and "patient" are used interchangeably.

In the present invention, it has been demonstrated that the presence of promoter methylation in the IGFBP-3 gene is indicative that the treatment to be administered is radiotherapy combined with cisplatin-based chemotherapy, whereas the absence of methylation in said promoter is indicative that the therapy to be administered is cisplatin-based chemotherapy only.

Therefore, a second aspect of the invention relates to an in vitro method to design an individualised treatment for a subject with cancer, which comprises detecting and/or quantifying the promoter methylation of the IGFBP-3 gene in a biological sample of said subject, such that the presence of methylation in said promoter is indicative that the treatment to be administered is radiotherapy combined with cisplatin-based chemotherapy.

The term "in vitro" refers to the fact that the method of the invention is performed outside the subject's body.

A preferred embodiment of the first and second aspects of the invention relates to the method wherein the detection and/or quantification of the promoter methylation of the IGFBP-3 gene are performed in the promoter region located between positions −584 and −492 of the promoter, both positions included (SEQ ID NO: 2).

In the present invention, the location of positions −584 and −492 of the IGFBP-3 gene promoter is determined from the ATG start codon, in accordance with the method used by persons skilled in the art.

Another, even more preferred embodiment of the first and second aspects of the invention relates to the method wherein the detection and/or quantification of the promoter methylation of the IGFBP-3 gene is performed at positions −532 and −526 from the ATG start codon. I.e. these positions correspond to positions 157 and 163 of SEQ ID NO: 1, and to positions 53 and 59 of SEQ ID NO: 2. Positions −532 and −526 are cytosines contained in CG dinucleotides.

Another, even more preferred embodiment of the first and second aspects of the invention relates to the method wherein the detection and/or quantification of the promoter methylation of the IGFBP-3 gene are performed by means of a polymerase chain reaction. Preferably, the polymerase chain reaction involves using the primer pairs SEQ ID NO: 3 (sense primer, with the sequence 5'-ttttacgaggtatatac-gaatgc-3') and SEQ ID NO: 4 (anti-sense primer, with the sequence 5'-tctcgaaataaaatctccctacg-3') (primers designed for the detection of methylation), and/or SEQ ID NO: 5 (sense primer, with the sequence 5'-agaaagttttatgagg-tatatga-3') and SEQ ID NO: 6 (anti-sense primer, with the sequence 5'-cactctcaaaataaaatctccct-3') (primers designed for the detection of absence of methylation). Preferably, the polymerase chain reaction involves using the primer pairs SEQ ID NO: 3 and SEQ ID NO: 4.

As used herein, the term "primer" (also called "oligo") refers to an oligonucleotide that is capable of acting as the starting-point for DNA synthesis when it hybridises to the nucleic acid matrix. Preferably, the primer is a deoxyribose oligonucleotide. The primers may be prepared by means of any suitable method, including, for example, without being limited thereto, the cloning and restriction of appropriate sequences and direct chemical synthesis. The primers may be designed such that they hybridise to specific nucleotide sequences in the nucleic acid matrix (specific primers) or randomly synthesised (arbitrary primers).

As specified above, the method of the invention may also be performed by using a probe, in which case it would be a quantitative method; on the contrary, if only the primers are used, but not a probe, it would be a semi-quantitative method.

Therefore, another, even more preferred embodiment of the first and second aspects of the invention relates to the method wherein a nucleic acid probe that comprises nucleotide sequence SEQ ID NO: 7 (5'-ccgatatcgaaaaaact-3') is further used. Preferably, the probe is nucleotide sequence SEQ ID NO: 7. More preferably, the probe comprises a fluorophore, for example, FAM™ or VIC®, at the amino-terminal end and/or at the carboxy-terminal end. In an even more preferred embodiment, the probe comprises the fluorophore 6-FAM™ at the amino-terminal end and a non-fluorescent minor groove binder (MGB), MGB-NFQ, at the carboxyl terminal.

In the present invention, we will refer to nucleotide sequence SEQ ID NO: 7 as the "probe of the invention".

The probe of the invention may be produced by means of methods known to persons skilled in the art. For example, it may be produced through chemical synthesis.

The probe of the invention binds to the DNA of the IGFBP-3 gene promoter when it is methylated.

A third aspect of the present invention relates to an in vitro method to predict the response of a subject with cancer to treatment with radiotherapy combined with cisplatin-based chemotherapy, characterised in that it comprises the following steps:
  a. isolation of deoxyribonucleic acid in a biological sample isolated from a subject;
  b. modification of the isolated deoxyribonucleic acid by means of sodium bisulfite;
  c. hybridisation using specific primers;
  d. amplification of a sequence located between the primers described in step (c);
  e. detection of the promoter methylation of the IGFBP-3 gene;

f. comparing the methylation of step (d) with standard levels;
g. finding significant differences in the comparison of step (f);
h. associating the significant differences of step (g) to promoter methylation or demethylation of the IGFBP-3 gene;
i. associating the presence of methylation in step (h) with a favourable response to treatment with radiotherapy combined with cisplatin-based chemotherapy; or associating the demethylation in step (h) to an unfavourable response to treatment with radiotherapy combined with cisplatin-based chemotherapy.

In the present invention, the isolation of the DNA and the modification of the isolated deoxyribonucleic acid by means of sodium bisulfite are performed by methods known to persons skilled in the art.

As understood in the present invention, the term "standard levels" refers, for example, without being limited thereto, to the methylation levels obtained from a reference sample that presents a known degree of methylation.

In the present invention, "significant difference" refers to the fact that there are statistical differences between the compared values, the statistical probability being at least greater than 0.05 ($p>0.05$) or greater than 0.005 ($p>0.005$), as obtained according to the statistical test applicable to each case.

In the present invention, the terms "demethylation", "absence of methylation" and "lack of methylation" are used interchangeably.

In the present invention, "favourable" is considered to be an increased survival of the individual following the treatment. "Unfavourable" is considered to be a decreased survival of the individual following the treatment.

A preferred embodiment of the third method of the invention relates to the method wherein the reference sample and the study samples have been normalised prior to the comparison.

"Normalisation" is understood to mean the use of a control sample that makes it possible to eliminate experimental variations between the different samples.

A preferred embodiment of the third aspect of the invention relates to the method wherein the primers of step (c) are the primer pairs SEQ ID NO: 3 and SEQ ID NO: 4, and/or SEQ ID NO: 5 and SEQ ID NO: 6.

An even more preferred embodiment of the third aspect of the invention relates to the method wherein the primers of step (c) are SEQ ID NO: 3 and SEQ ID NO: 4.

Another, even more preferred embodiment of the third aspect of the invention relates to the method wherein step (c) further includes a probe and wherein the methylation is quantified in step (e). Preferably, the probe comprises nucleotide sequence SEQ ID NO: 7. More preferably, the probe is nucleotide sequence SEQ ID NO: 7.

Another, even more preferred embodiment of the third aspect of the invention relates to the method wherein the cancer is lung cancer, ovarian cancer, head and neck cancer, glioma or breast cancer. Preferably, the lung cancer is non-microcytic lung cancer.

A preferred embodiment of the first, second and third aspects of the invention relates to the method wherein the biological sample is selected from the group formed by tissue, blood, plasma, serum, lymph, broncho-alveolar lavage, saliva, urine and ascitic fluid.

Another preferred embodiment of the first, second and third aspects of the invention relates to the method wherein the biological sample is fresh, frozen, fixed or fixed and embedded in paraffin.

A fourth aspect of the present invention relates to a nucleic acid probe which comprises nucleotide sequence SEQ ID NO: 7.

A preferred embodiment of the fourth aspect of the invention relates to a nucleic acid probe which is nucleotide sequence SEQ ID NO: 7.

Another, even more preferred embodiment of the fourth aspect of the invention relates to the probe which further comprises a fluorophore, for example FAM™ or VIC®, at the amino-terminal end and/or the carboxy-terminal end. In an even more preferred embodiment, the probe comprises the fluorophore 6-FAM™ at the amino-terminal end and a non-fluorescent minor groove binder" (MGB), MGB-NFQ, at the carboxyl terminal.

A fifth aspect of the present invention relates to the in vitro use of the probe of the invention for the detection and/or quantification of the promoter methylation of the IGFBP-3 gene in a biological sample from a subject.

A sixth aspect of the present invention relates to the in vitro use of the probe of the invention to determine the response of a subject to treatment with radiotherapy combined with cisplatin-based chemotherapy.

A preferred embodiment of the fifth and sixth aspects of the invention relates to the use wherein the subject has cancer. Preferably, the cancer is lung cancer, ovarian cancer, head and neck cancer, glioma and breast cancer. More preferably, the lung cancer is non-microcytic lung cancer.

Another preferred embodiment of the fifth and sixth aspects of the invention relates to the use wherein the biological sample is selected from the group formed by tissue, blood, plasma, serum, lymph, broncho-alveolar lavage, saliva, urine and ascitic fluid.

Another preferred embodiment of the fifth and sixth aspects of the invention relates to the use wherein the biological sample is fresh, frozen, fixed or fixed and embedded in paraffin.

A seventh aspect of the invention relates to a kit that comprises the probe of the fourth aspect of the invention.

A preferred embodiment of the seventh aspect of the invention relates to the kit which further comprises primers. More preferably, the primers are the primer pairs SEQ ID NO: 3 and SEQ ID NO: 4, and/or SEQ ID NO: 5 and SEQ ID NO: 6.

The kit may further comprise at least one DNA polymerase, one reverse transcriptase, one RNA polymerase or one fluorophore. The kit may further comprise a mixture of de-oxynucleotide triphosphates (dNTPs), a mixture of nucleotide triphosphates (NTPs), deoxyribonuclease (DNase), ribonuclease (RNase) inhibitors, dithiothreitol (DTT), inorganic pyrophosphatase (iPP) and the necessary buffers for the enzymes supplied in the kit.

In the present invention, the probe or the primers may be located on a solid support, for example, without being limited thereto, glass, plastic, tubes, multiple-well plates, membranes or any other known support.

An eighth aspect of the invention relates to the in vitro use of the kit of the seventh aspect of the invention to determine and/or quantify the promoter methylation of the IGFBP-3 gene in a biological sample from a subject.

A ninth aspect of the invention relates to the in vitro use of the kit of the seventh aspect of the invention to predict the response of a subject to treatment with radiotherapy combined with cisplatin-based chemotherapy.

A preferred embodiment of the eighth and ninth aspects of the invention relates to the use wherein the subject has cancer. Preferably, the cancer is lung cancer, ovarian cancer, head and neck cancer, glioma or breast cancer. More preferably, the lung cancer is non-microcytic lung cancer.

Another preferred embodiment of the eighth and ninth aspects of the invention relates to the use wherein the biological sample is selected from the group formed by tissue, blood, plasma, serum, lymph, broncho-alveolar lavage, saliva, urine and ascitic fluid.

Another preferred embodiment of the eighth and ninth aspects of the invention relates to the use wherein the biological sample is fresh, frozen, fixed or fixed and embedded in paraffin.

Herein, the terms "nucleotide sequence", "polynucleotide", "nucleic acid" and "oligonucleotide" are used interchangeably and refer to polymers of nucleotides. Said nucleotides may or may not be chemically or biochemically modified.

Throughout the description and the claims, the word "comprises" and variants thereof are not intended to exclude other technical characteristics, additives, components or steps. For persons skilled in the art, other objects, advantages and characteristics of the invention will arise, partly from the description and partly from the practice of the invention. The following examples and figures are provided for illustrative purposes, and are not intended to limit the scope of the present invention.

EXAMPLES

Figure 1:
FIG. 1 shows the methylation status of each CpG position analysed in the CpG island that comprises the IGFBP-3 gene promoter and its frequency of methylation in non-tumoural or non-neoplastic DNA. The transcription start codon (ATG) and the TATA box (TATA) are indicated. A, tumoural DNA; B, non-neoplastic DNA from control tissue. The arrows show the location of the primers and the probe of the invention, which only detects the presence of methylated DNA. Black circles: high frequency of methylation, >30%; grey circles: moderate frequency of methylation, 15%-30%; white circles: low frequency of methylation, 0%-15%.
Figure 1:
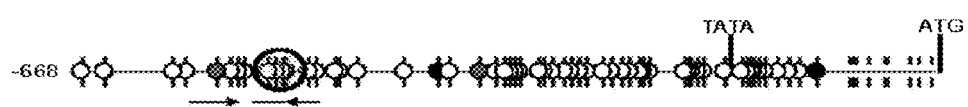

Quantitative Methylation Assay:

In order to evaluate the methylation status of the IGFBP-3 gene in each sample, the genomic DNA sequence was first modified through the combined use of sodium bisulfite and hydroquinone. The modified DNA was amplified by means of fluorescence-based real-time PCR according to a previously described protocol (Harden S. V. et al. 2003 Clin Cancer Res 8:1370-5).

The oligos used in the present invention were previously described (Ibáñez de Cáceres I. et al. 2010 Oncogene 29: 1681-1690). The use of these oligos (also called "primers" in the present invention) makes it possible to identify the presence of methylation in the promoter zone of the IGFBP-3 gene by means of the methylation-specific PCR (MSP) technique, which is a semi-quantitative technique. The primers are the pair SEQ ID NO: 3 and SEQ ID NO: 4, which detects methylation; and the pair SEQ ID NO: 5 and SEQ ID NO: 6, which detects the absence of methylation.

The use of the probe of the invention (SEQ ID NO: 7) made it possible to quantify the promoter methylation of the IGFBP-3 gene by means of the quantitative MSP (QMSP) technique.

Numerous assays were performed on a panel of 26 human cancer cell lines, by modifying the DNA, eliminating the non-methylated cytosines and substituting them with uracils, followed by amplification and sequencing of the DNA area comprised between both oligos, in order to identify the CpG nucleotide positions most frequently methylated, in an unaltered, constant manner, when the gene is deactivated. This made it possible to identify the region-specific methylation for modified DNA between positions −584 and −492 of the IGFBP-3 gene promoter, and to select the adequate labeling at the 5' and 3' ends, in order to produce a probe that would prove effective for the technique. The product amplified by means of this technique (called "QMSP-IGFBP-3") is quantitatively detected by using the specific probe of the present invention (SEQ ID NO: 7), labelled with the fluorochrome FAM™ at the 5' end and with a non-fluorescent minor groove binder (MGB), NFQ, at the 3' end (6FAM5'-CCGA-TATCGAAAAAACT-3'MGB-NFQ). Following the binding, this probe generated a fluorescence signal, which made it possible to quantify the levels of the PCR-amplified methylated product. The quantification of the degree of methylation of the IGFBP-3 gene is exclusively dependent on the specificity of the probe of the invention and not on the QMSP technique itself. The QMSP technique described in the present invention to detect the methylation of the IGFBP-3 gene was called "QMSP-IGFBP-3".

Therefore, the QMSP-IGFBP-3 technique of the present invention is based on the fluorescence amplification of modified DNA, which makes it possible to quantify the promoter methylation of the IGFBP-3 gene in bisulfite-modified DNA samples. The relative levels of DNA with promoter methylation of the IGFBP-3 gene ("relative methylation levels") in each sample were determined as a ratio between the values obtained from the amplification of the selected region of the IGFBP-3 gene promoter and those obtained from the amplification of the β-actin gene, used as an endogenous reference. The ratio was multiplied by 1000 in order to facilitate its tabulation (gene of interest/reference gene ×1000), to obtain a methylation quotient (MQ) that represents the relative methylation level of the study sample, as has been described for other genes (Eads C. A. et al. 2000 Nucleic Acid Res 28:E32; Eads C. A. et al. 1999 Cancer Res 59:2302-6).

In our methylation analysis, the amplifications were performed in 96-well plates in the StepOnePlus™ amplicon-detection system, from the company Applied Biosystems, with a final volume of 25 μl in each well, containing:

600 nM of each primer designed for the amplification of the modified DNA methylated for the IGFBP-3 gene; 200 nM of specific probe; 2× TaqMan Universal Master Mix II, a reaction that contains AmpliTaq Gold® DNA Polymerase, Uracil-N glycosylase (UNG), dNTPs with dUTP, and ROX™ as a reference, jointly with an optimised buffer, all from the company Applied Biosystems; and modified DNA, where 3 μl of treated DNA were used for each QMSP reaction. The QMSP reaction conditions were the following; 1 2-minute cycle at 50° C.; 1 10-minute cycle at 95° C. and 50 15-second cycles at 95° C. and 1-minute cycles at 60° C., in a final volume of 25 μl. The MSP conditions had been previously described (Ibáñez de Cáceres I., el al. 2012 Oncogene 29:1681-1690).

Each plate contained the tumoural samples, numerous water blanks (NTCs), and positive and negative controls. DNA from the human cancer lines SW780 (bladder), HT29 (colon) and 41MR (ovary) was used as a positive control, since these lines present promoter methylation of the IGFBP-3 gene. Serial dilutions of a pool of these modified DNAs, ranging from 30 ng/μl to 0.003 ng/μl, served as a control for the standard curves of β-actin and IGFBP-3 in each plate used for each assay.

In each assay, the sensitivity and specificity were determined for a range of threshold values in both standard curves, and an ideal threshold was selected which would differentiate the true positive cases (regardless of the methylation levels in each sample) from the true negative cases. All the true negative cases in the technology that we present were validated as negative by means of the bisulfite sequencing (BS) and/or the methylation-specific PCR (MSP) techniques, which would correspond to 100% specificity.

A sample was considered to be positive for methylation when the value of MQ is greater than 1. This value is obtained for the methylated IGFBP-3 gene promoter in each sample, and is determined as a ratio between the values obtained from the amplification of the selected region of the IGFBP-3 gene promoter and those obtained from the amplification of the β-actin gene, used as an endogenous reference. The ratio is multiplied by 1000 in order to facilitate its tabulation (gene of interest/reference gene ×1000), to obtain a methylation quotient (MQ) that represents the relative methylation level of the study sample, as has been described for other genes, such as MGMT, APC, MLH1 and p16 (Durr M. L. et al. PLoS One 2010 May 26; 5(5):e10828).

Results

Figure 2:
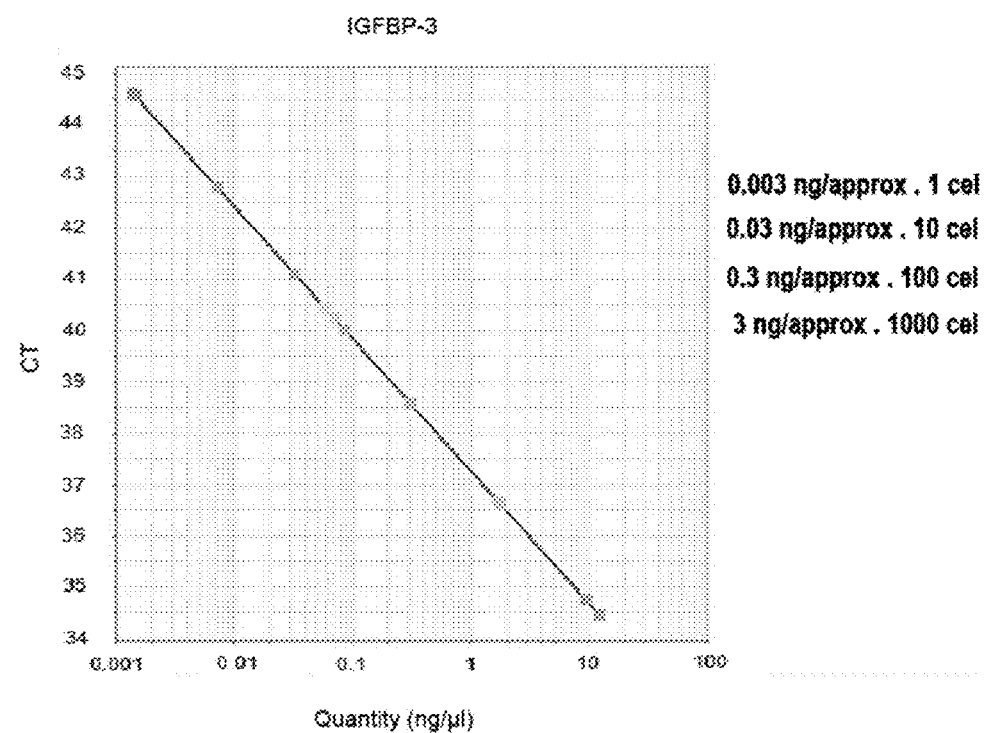
FIG. 2 shows the standard quantitative curves for the IGFBP-3 (A) and β-actin (B) genes from four serial dilutions of bisulfite-modified DNA (3 ng-0.003 ng). The amplified product is quantitatively detected by using the probe of the invention, which generates a fluorescence signal that makes it possible to quantify the levels of PCR-amplified methylated product in a region of the IGFBP-3 gene promoter, and allows for the amplification and, consequently, the quantification of the methylated DNA levels contained in the sample analysed for the IGFBP-3 gene, to a sensitivity of 1 methylated allele in a background of 10,000 non-methylated alleles (sensitivity 1:10,000). The data for each sample are normalised with those obtained from interpolation into the β-actin curve. "approx", approximate; "cel" cell; CT, "cycle threshold".

The design of the primers and the probe of the present invention are specific for the IGFBP-3 gene promoter region between positions −584 and −492, both included, and makes it possible to amplify and, consequently, quantify the methylated DNA levels contained in the sample analysed for the IGFBP-3 gene, to a sensitivity of 1 methylated allele in a background of 10,000 non-methylated alleles (sensitivity 1:10,000) (FIG. 1). The standard curves for the identification of the methylation of the IGFBP-3 gene meet the expected linearity and parallelism with respect to the standard curves for the β-actin reference gene. As an example, in FIG. 2, we show both curves obtained in the same experimental process.

Figure 3:
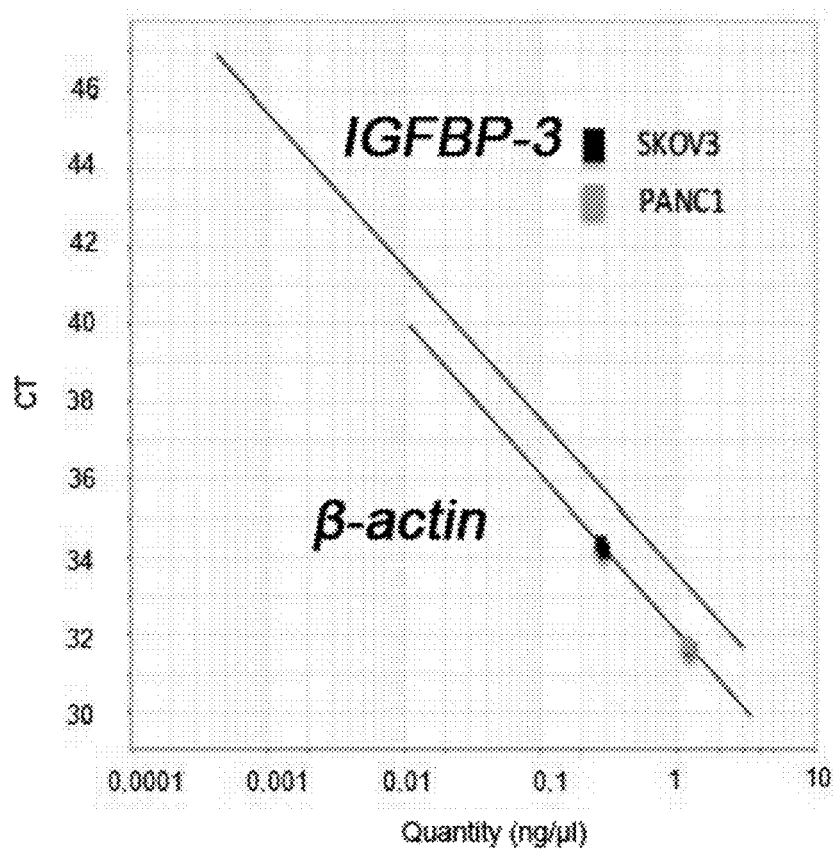
FIG. 3 shows standard curves designed to identify the methylated IGFBP-3 gene. It shows the expected linearity between the standard curves for the identification of the methylated IGFBP-3 gene and the standard curves for the β-actin reference gene, and the interpolation of the positive-control DNAs (SW780 and HT29) (A) and the negative-control DNAs (SKOV3 and PANC1) (B). A, interpolation of the positive-control cell lines (SW780 and HT29) into the respective curves for the methylated IGFBP-3 gene and for β-actin as the non-methylated endogenous control, whereas (B) shows that the negative-control lines (SKOV3, from breast cancer, and PANC1, from pancreas cancer) only interpolate into the curve for β-actin as the non-methylated endogenous control. These results confirm the specificity of the methodology of the invention.

The new methodology was tested in the human cancer lines that served as controls, since they were the ones used for identification of the probe. Their methylation status for the IGFBP-3 gene was tested using both the bisulfite sequencing technique and the methylation-specific PCR technique (MSP). In FIG. 3, the left-hand panel shows a clear interpolation of the positive-control cell lines (SW780 and HT29) into the respective curves for the methylated IGFBP-3 gene and for β-actin, used as the non-methylated endogenous control, whereas the right-hand panel shows that the negative-control lines (SKOV3, from breast cancer, and PANC1, from pancreas cancer), only interpolate into the curve for β-actin, used as the non-methylated endogenous control. These results confirm the specificity of the methodology presented in this invention (FIG. 3).

Figure 4:
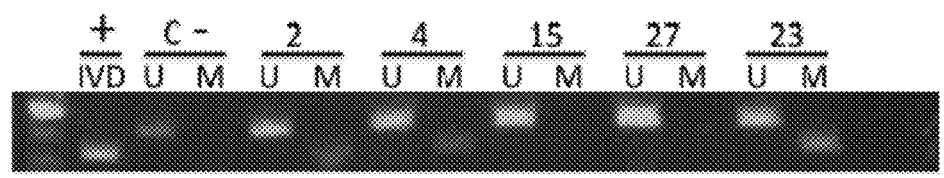
FIG. 4 shows a comparison of the sensitivity and specificity of the quantitative detection of the promoter methylation of the IGFBP-3 gene by means of the probe of the invention using QMSP and using the traditional MSP technique in a cohort of samples from patients with NMLC preserved in paraffin. It shows an example of a gel from the MSP technique that includes positive controls (IVD), negative controls (C−) and water, which confirms that patients 2, 4 and 23 are methylated, and that the methylation in patients 15 and 27 is not detected using this technique, whereas, when using QMSP, we were able to detect the presence of methylation in these patients.

Subsequently, the sensitivity and specificity of this new QMSP-IGFBP-3 technology was compared to the traditional MSP technique in two series of samples from patients with NMLC preserved in paraffin. The first cohort of patients demonstrated the specificity of the technique presented (QMSP-IGFBP-3), as compared to the traditional MSP technique (described in Ibáñez de Cáceres I. et al. 2010 Oncogene 29:1681-1690). In 28 of 32 patients with NMLC subjected to extirpation at the La Paz University Hospital, we found the same methylation status for the IGFBP-3 gene using both techniques, and the remaining 4 patients were rescued, because the presence of methylation was not found using the traditional MSP technique, and the samples were first identified as non-methylated, whereas, when using the probe of the invention, it was possible to identify the presence of a moderate degree of methylation in these 4 samples from patients, since the sensitivity increases by one order of magnitude (Table 1, with an asterisk). Moreover, this technique incorporates values for the degree of methylation, as it is a quantitative evaluation; this allows for continuous-variable correlation studies and the statistical value increases. In FIG. 4, we show, as an example, a gel from the MSP technique that includes positive controls (IVD), negative controls (C−) and water, which confirms that patients 2, 4 and 23 are methylated, and that the methylation in patients 15 and 27 is not detected by means of this technique, whereas, when using QMSP with the probe of the invention, we were able to detect presence of methylation in these patients.

TABLE 1

Results obtained for MSP and for the qMSP of the present invention in tissues from patients.

| Sample | Anatomic Pathology | TNM | Stage | MSP | qMSP (RQ, relative methylation level) |
|---|---|---|---|---|---|
| 1 | Large-cell | T2N1 | 2B | M | M (0.55) |
| 2 | Epidermoid | T2N0 | 1B | M | M (0.15) |
| 3 | Epidermoid | T2N1 | 2B | U | * M (12.95) |
| 4 | Epidermoid | T3N0M0 | 2B | M | M (10.84) |
| 5 | Epidermoid | T2N0M0 | 1B | M | M (3.9) |
| 6 | Adenocarcinoma | T1N0M0 | 1A | U | U |
| 7 | Epidermoid | T1N0M0 | 1A | U | U |
| 8 | Epidermoid | T2N0 | 1B | M | M (0.22) |
| 9 | Large-cell | T1N0M0 | 1A | M | M (0.046) |
| 10 | Adenocarcinoma | Unknown | Unknown | M | M (11.3) |
| 11 | Adenocarcinoma | T2N0M0 | 1B | M | M (0.30) |
| 12 | Adenocarcinoma | T1N0M0 | 1B | M | M (0.2) |
| 13 | Epidermoid | T2N0M0 | 1B | U | U |
| 14 | Epidermoid | T2N0 | 1B | M | M (54.9) |
| 15 | Adenocarcinoma | T2N0 | 1B | U | * M (0.14) |
| 16 | Epidermoid | T2N0M0 | 1B | U | U |
| 17 | Adenocarcinoma | T2N0M0 | 1B | U | U |
| 18 | Adenocarcinoma | T3N0 | 2B | U | U |
| 19 | Epidermoid | T2N1 | 2B | U | * M (2.6) |
| 20 | Epidermoid | T2N0 | 1B | U | U |
| 21 | Epidermoid | T3N0 | 2B | U | U |
| 22 | Epidermoid | T2N2 | 3A | U | U |
| 23 | Epidermoid | T2N0 | 1B | M | M (4.9) |
| 24 | Epidermoid | Unknown | Unknown | U | U |
| 25 | Epidermoid | T3N0 | 2A | M | M (91.6) |
| 26 | Epidermoid | T2N1 | 2B | U | U |
| 27 | Epidermoid | T2N1 | 2B | U | * M (0.7) |
| 28 | Adenocarcinoma | T2N1 | 2B | U | U |
| 29 | Large-cell | T2N0 | 1B | U | U |
| 30 | Epidermoid | T2N1 | 2B | U | U |

TABLE 1-continued

Results obtained for MSP and for the qMSP of the present invention in tissues from patients.

| Sample | Anatomic Pathology | TNM | Stage | MSP | qMSP (RQ, relative methylation level) |
|---|---|---|---|---|---|
| 31 | Adenocarcinoma | T2N1 | 2B | U | U |
| 32 | Epidermoid | T1N0 | 1A | U | U |

TNM, lung cancer classification.
"RQ", relative quantification;
U, non-methylated;
M, methylated.

Figure 5:
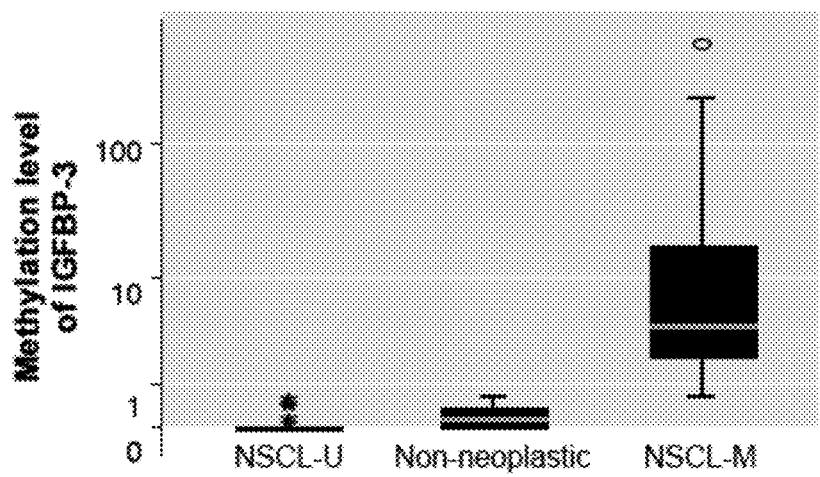
FIG. 5 shows the methylation levels of IGFBP-3 in a second cohort of 40 patients and ten non-neoplastic samples, and the Kaplan-Meier overall survival curve, represented in days, for patients with non-methylated IGFBP-3 subjected to a treatment with chemotherapy or chemotherapy-radiotherapy. (A), Methylation levels of IGFBP-3 in a second cohort of 40 patients and ten non-neoplastic samples, by means of the IGFBP-3/ACTB ratios. NSCLC-M: samples of non-microcytic lung cancer considered to be methylated for IGFBP-3; NSCLC-U: samples of non-microcytic lung cancer considered to be non-methylated for IGFBP-3. (B) Kaplan-Meier curves, comparing the methylation status of non-methylated IGFBP-3 with the cumulative survival, in days, of 40 patients with NMLC subjected to a treatment with chemotherapy or a combined treatment of chemotherapy-radiotherapy. Those patients whose survival could not be followed beyond the time indicated for the censoring were censored. "Radiotherapy +" means treatment with radiotherapy; "Radiotherapy −" means that there is no treatment with radiotherapy.
Figure 5:
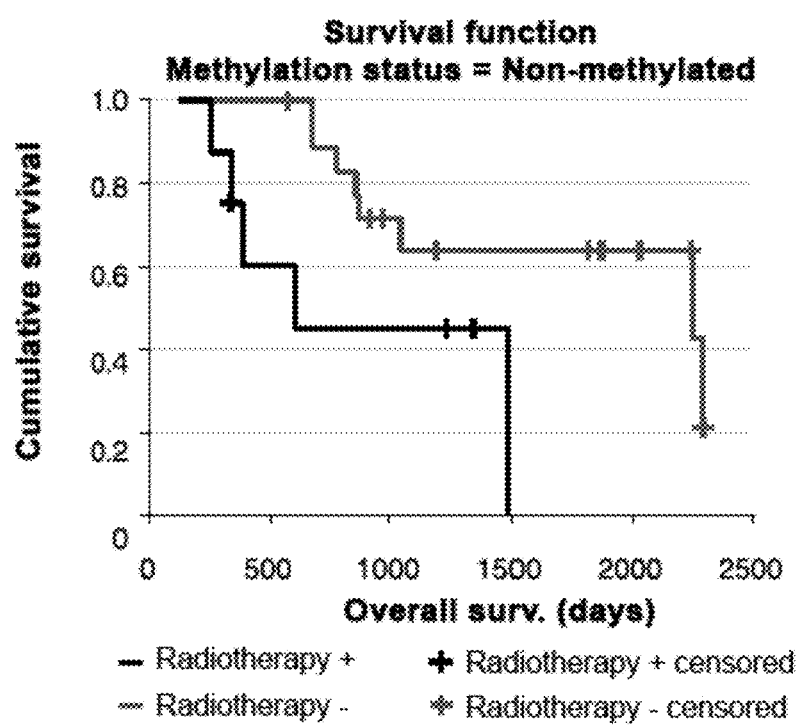

Moreover, in a second, confirmatory series with 40 tumour pieces embedded in paraffin from patients with NMLC subjected to extirpation at the Del Mar Hospital in Barcelona, we confirmed the sensitivity of the technique for the identification of the presence and the degree of methylation, and demonstrated, in the first place, that the range of values was similar to that obtained for the first cohort. All the patients interpolated into the curve of the non-methylated β-actin endogenous control, which guarantees the presence of the modified DNA under study, whereas 21 of the 40 patients also interpolated into the curve for the methylated IGFBP-3 gene, resulting in relative values for the presence of methylated DNA for the IGFBP-3 gene with different degrees of methylation (reflected in the value in parentheses and called "relative methylation level"), with approximate methylation quotient (MQ) values ranging between 0.01 and 100 (FIG. 5A). The MQ values obtained are similar to those obtained for the initial cohort from the La Paz U H (FIG. 4 and Table 1). In the second place, it was demonstrated that the absence of promoter methylation in the IGFBP-3 gene is indicative that the treatment to be administered is chemotherapy with cisplatin, instead of combined chemo-radiotherapy (FIG. 5B); for this reason, patients who present absence of methylation should not receive radiotherapy, since the overall survival rate of patients with non-methylated IGFBP-3 who receive only chemotherapy is greater than that of those who receive combined treatment with chemotherapy and radiotherapy.

Therefore, the technique is capable of identifying the presence of methylated DNA within a broad range (FIG. 5A). These results meet an existing need, thus far unresolved in clinical practice, i.e. identifying which patients present a high probability of responding to a treatment with radiotherapy combined with chemotherapy based on platinum derivatives, such as cisplatin, carboplatin, oxaliplatin, satraplatin, etc.

The invention claimed is:

1. A nucleic acid probe which consists of the nucleotide sequence SEQ ID NO: 7 and a fluorophore at the 5' end and/or at the 340 end for detecting and/or quantifying the promoter methylation of the IGFBP-3 gene at positions −532 and −526 of the promoter.

* * * * *